(12) United States Patent
Eldar et al.

(10) Patent No.: US 7,947,054 B2
(45) Date of Patent: May 24, 2011

(54) MESH DEPLOYMENT APPARATUS

(75) Inventors: Samuel Eldar, Haifa (IL); Shalom Levin, Atlit (IL); Izhak Fabian, Kfar Truman (IL)

(73) Assignee: EasyLab Ltd., Kfar Truman (IL)

( * ) Notice: Subject to any disclaimer, the term of this patent is extended or adjusted under 35 U.S.C. 154(b) by 409 days.

(21) Appl. No.: 11/674,683

(22) Filed: Feb. 14, 2007

(65) Prior Publication Data
US 2008/0195121 A1 Aug. 14, 2008

(51) Int. Cl.
*A61B 17/03* (2006.01)
*A61B 17/08* (2006.01)

(52) U.S. Cl. ...................................................... 606/151

(58) Field of Classification Search .................. 606/151, 606/213, 1, 108; 623/23.72, 23.73, 23.74, 623/23.75, 23.76, 1.11; 600/141, 142, 146, 600/147, 37; 242/348, 588.6, 606, 608, 614; 206/225, 576; 604/13, 15, 264, 261
See application file for complete search history.

(56) References Cited

U.S. PATENT DOCUMENTS

| | | | | |
|---|---|---|---|---|
| 1,171,545 A | * | 2/1916 | Sands | 242/604 |
| 4,839,215 A | * | 6/1989 | Starling et al. | 428/131 |
| 5,147,387 A | * | 9/1992 | Jansen et al. | 606/108 |
| 5,263,969 A | | 11/1993 | Phillips | |
| 5,304,187 A | * | 4/1994 | Green et al. | 606/151 |
| 5,370,650 A | * | 12/1994 | Tovey et al. | 606/151 |
| 5,397,331 A | * | 3/1995 | Himpens et al. | 606/151 |
| 5,464,403 A | * | 11/1995 | Kieturakis et al. | 606/1 |
| 5,503,623 A | * | 4/1996 | Tilton, Jr. | 604/13 |
| 5,667,522 A | * | 9/1997 | Flomenblit et al. | 606/198 |
| 5,766,157 A | * | 6/1998 | Tilton, Jr. | 604/264 |
| 5,797,899 A | * | 8/1998 | Tilton, Jr. | 606/1 |
| 5,919,184 A | * | 7/1999 | Tilton, Jr. | 606/1 |
| 5,957,939 A | | 9/1999 | Heaven et al. | |
| 6,010,495 A | * | 1/2000 | Tilton, Jr. | 606/1 |
| 6,156,045 A | * | 12/2000 | Ulbrich et al. | 606/151 |
| 6,258,113 B1 | * | 7/2001 | Adams et al. | 606/192 |
| 6,478,803 B1 | * | 11/2002 | Kapec et al. | 606/151 |
| 6,638,292 B2 | * | 10/2003 | Adams | 606/192 |
| 6,783,554 B2 | * | 8/2004 | Amara et al. | 623/23.76 |
| 6,932,836 B2 | * | 8/2005 | Amin | 623/1.11 |
| 7,377,906 B2 | * | 5/2008 | Selkee | 604/95.04 |
| 2007/0112361 A1 | * | 5/2007 | Schonholz et al. | 606/151 |

FOREIGN PATENT DOCUMENTS

| | | | |
|---|---|---|---|
| EP | 0557963 | | 9/1993 |
| WO | WO 92/06638 | * | 4/1992 |
| WO | WO92/06638 | * | 4/1992 |
| WO | WO01/89390 | | 11/2001 |
| WO | WO2004/080348 | | 9/2004 |
| WO | WO 2006/082587 | * | 8/2006 |
| WO | WO2007/030676 | | 3/2007 |

* cited by examiner

*Primary Examiner* — Julian W Woo
*Assistant Examiner* — Christopher L Templeton
(74) *Attorney, Agent, or Firm* — Dekel Patent Ltd; David Klein (57) ABSTRACT

Mesh deployment apparatus including a deployment rod having a proximal handle and a distal roller portion, the roller portion having a mesh-sheet attachment member to which a mesh-sheet is attached. The roller portion is articulated with respect to the deployment rod by means of a joint, and a manipulating member is coupled to the roller portion for moving the roller portion about the joint to a position such that the roller portion is not collinear with the deployment rod.

12 Claims, 12 Drawing Sheets

MESH DEPLOYMENT APPARATUS

FIELD OF THE INVENTION

The present invention generally relates to a device and method for the deployment and placement of a mesh-sheet in a body, such as for hernia repair in a laparoscopic procedure.

BACKGROUND OF THE INVENTION

Hernias are abnormal protrusions of an organ (or organs) through a defect or natural opening in a covering membrane, muscle or bone. Most hernias protrude in the inguinal region as inguinal (direct or indirect) or femoral hernias and in the anterior abdominal wall region, as incisional, umbilical, epigastric or Spigelian hernias.

Hernia repair may require surgery. A small defective gap may be closed by sutures, and in cases of a larger defective gap, a mesh-sheet (or mesh, for short) may be applied over the gap. In some cases a mesh-sheet may be used for reinforcing a primary sutured defect in the abdominal wall. The mesh-sheet is fixed with sutures at peripheral edges thereof to the abdominal wall.

Tools have been developed to assist deploying and placing mesh-sheets in a laparoscopic procedure. For example, U.S. Pat. No. 5,464,403 describes a tool for the placement of a flexible sheet in laparoscopic procedures. The tool includes an elongate tubular assembly and an elongate tubular member having a bore. A rod is disposed in the bore and terminates short of the distal extremity of the elongate tubular assembly. A rotatable member is secured to the proximal extremity of the rod. A handle is secured to the proximal extremity of the elongate tubular assembly and receives the rotatable member. The tubular assembly has a slot extending longitudinally which permits access to the annular chamber and the extremity of the rod. The distal extremity of the rod engages one edge of the sheet, hence as the rod is rotated in one direction, the sheet of mesh unwound from the rod and into the patient.

U.S. Pat. No. 5,957,939 describes a medical device for deploying surgical fabric such as mesh-sheet within a body cavity of a patient. The device includes a deploying member and a clamping member supported at the distal end of the deploying member for holding the fabric in rolled and unrolled configurations. The clamping member is engageable with a portion of a piece of surgical fabric and rotatable with respect to the deploying member so that the fabric in the unrolled configuration can be wrapped around the clamping member to the rolled configuration. The device further includes a self-unwinding member at the distal end of the deploying member, the self-unwinding member being effective in automatically unwinding the fabric from the rolled configuration to the unrolled configuration.

The above mentioned patents refer to means for deploying a mesh sheet but no reference is made to placing the mesh-sheet in its position within the abdominal cavity.

PCT published patent application WO 2004/080348 to the present inventor, the disclosure of which is incorporated herein by reference, describes apparatus that includes a rod formed with a handle portion and a coaxial roller portion. The mesh-sheet is wound around the roller portion. In one application the roller portion has a distal end provided with a tissue-anchoring stud. The roller portion may be rotatably attached to the handle portion. The rear edge of the mesh-sheet is detachably attached to the roller portion of the apparatus, such as with surgical threads or by any other means such as adhesive material, and the mesh-sheet is wound around the roller portion before use.

The roller portion of the rod with the mesh-sheet wound therearound is placed into a cannula and inserted through an incision into the body. The tissue-anchoring stud at the distal end of the roller portion is anchored to the tissues, e.g., by stabbing, which facilitates unrolling the mesh-sheet and positioning the rear edge of the mesh-sheet.

The mesh-sheet is placed within the abdominal cavity or inguinal space by pulling the surgical threads of the leading edge towards a pre-determined position within the cavity/space to thereby cover the hernial defect. This is achieved by suitable forceps used for manipulating the needles. The needles provided at the ends of the surgical threads are then used for stitching to the appropriate tissues of the patient, possibly by piercing the tissues of the patient from the abdominal cavity to the outside of the patient. During the stage of pulling the leading edge of the mesh-sheet by the surgical threads, the rod remains stationary and the roller rotates freely to enable smooth and easy deployment and positioning of the mesh-sheet over the hernial defect.

To conclude the hernia repair, the corners of the mesh-sheet are stitched to the body of the patient, or otherwise attached, e.g. by stapling, etc. and the surgical threads are cut and discarded. The mesh-sheet is then detached from the roller portion of the rod whereby the rod may be removed.

SUMMARY OF THE INVENTION

The present invention seeks to provide a device and method for the deployment and placement of a mesh-sheet in a body, e.g., the abdominal cavity or the inguinal space, such as for covering a hernial defect of a patient during a hernia repair in a laparoscopic procedure.

The device provides a user with great flexibility and the ability to spread the mesh at any orientation while keeping the rolled mesh axis parallel to its starting orientation all along the spreading process.

The present invention provides improvements over the device of PCT published patent application WO 2004/080348, by providing a joint that increases the possibilities of maneuvering the roller portion of the device, as is described in more detail hereinbelow.

The term hernia is used throughout the specification and claims to encompass any type of hernia, such as but not limited to, abdominal hernia (incisional, umbilical, epigastric or Spigelian), inguinal hernia (inguinal or femoral) and others. It is noted that the invention is not limited to repair of hernias and may be used for any medical procedure that requires some kind of deployment of a mesh.

The present invention may be used for abdominal hernia repairs of any of the aforementioned types, e.g., incisional, umbilical, Spigelian and epigastric hernias. Moreover, it is appreciated that the invention is applicable in a variety of similar operations, such as, for example inguinal hernias, etc (direct and indirect) and femoral hernias.

There is thus provided in accordance with an embodiment of the present invention mesh deployment apparatus including a deployment rod having a handle at a proximal portion thereof and a roller portion at a distal portion thereof, the roller portion having a mesh-sheet attachment member for attaching a mesh-sheet thereto, wherein the roller portion is articulated with respect to the deployment rod by means of a joint, and a manipulating member coupled to the roller portion for moving the roller portion about the joint to a position wherein the roller portion is not collinear with the deployment rod.

The manipulating member may include a lever arm mounted on the deployment rod. The manipulating member may be coupled to the roller portion with a linking member that runs through a lumen formed in the deployment rod. The linking member may rotate about pivots at the joint.

In accordance with an embodiment of the present invention, the roller portion may be actuated by a swing lever and a push pull rod mechanism that easily changes its relative angle with respect to the deployment rod, e.g., in a range of ±90°. The swing lever may have a zero position for easy insertion and extraction of the device from a trocar. By changing both the deployment rod relative angle to the patient's body and the roller portion relative angle, the surgeon can easily place the mesh anywhere at any orientation.

The manipulating member may be pivotally mounted on the deployment rod.

The roller portion may be disposed in a cannula. The roller portion may be mounted on bearings in the cannula. The roller portion may include a pair of end caps at opposite ends of a shaft, the end caps being formed with apertures for placing therethrough surgical threads of the mesh-sheet.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Reference is now made to FIGS. 1-6, which illustrate mesh deployment apparatus 10, constructed and operative in accordance with an embodiment of the present invention.

Figure 1:
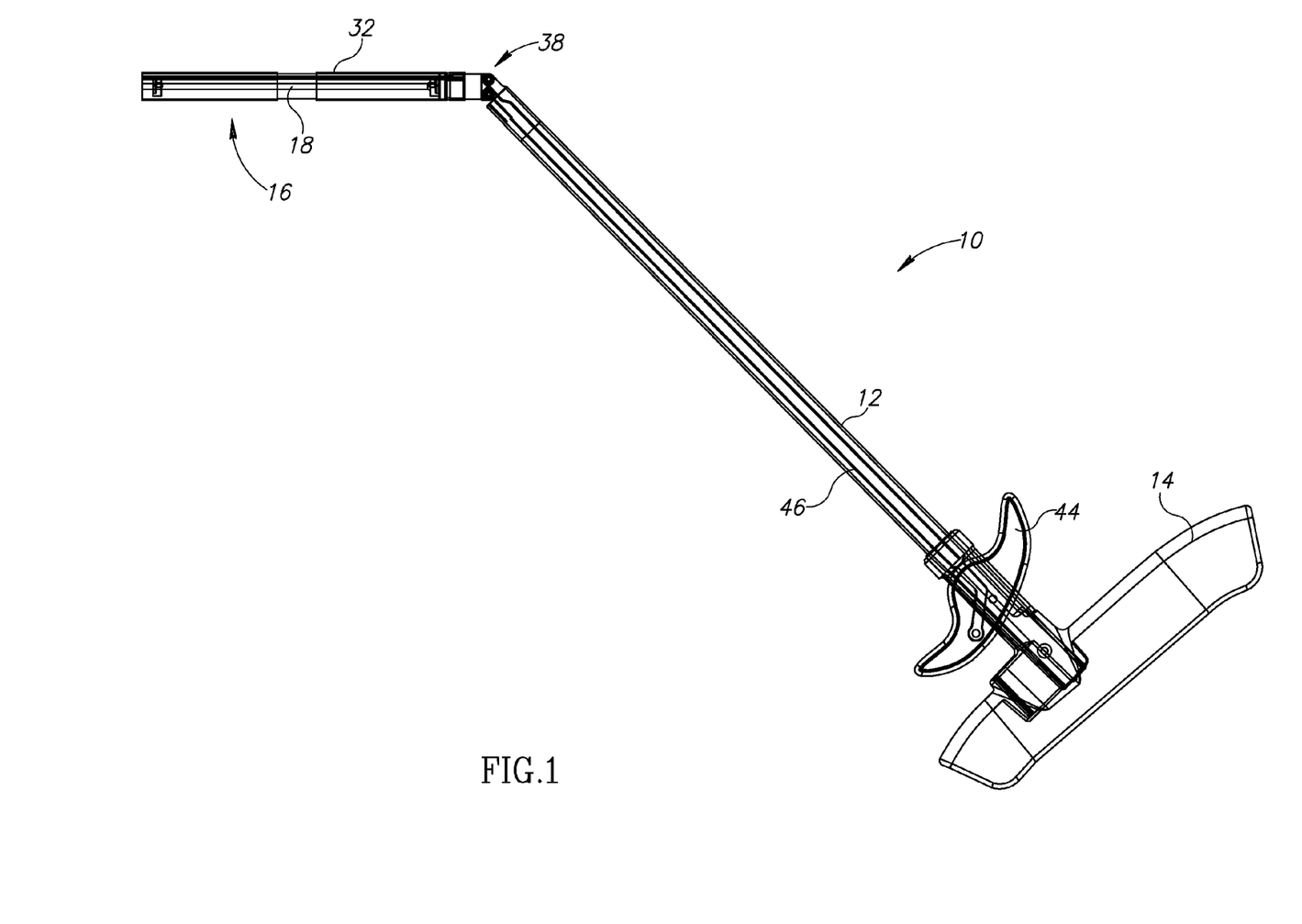
FIG. 1 is a simplified illustration of a mesh deployment apparatus, constructed and operative in accordance with an embodiment of the present invention.
Figure 2:
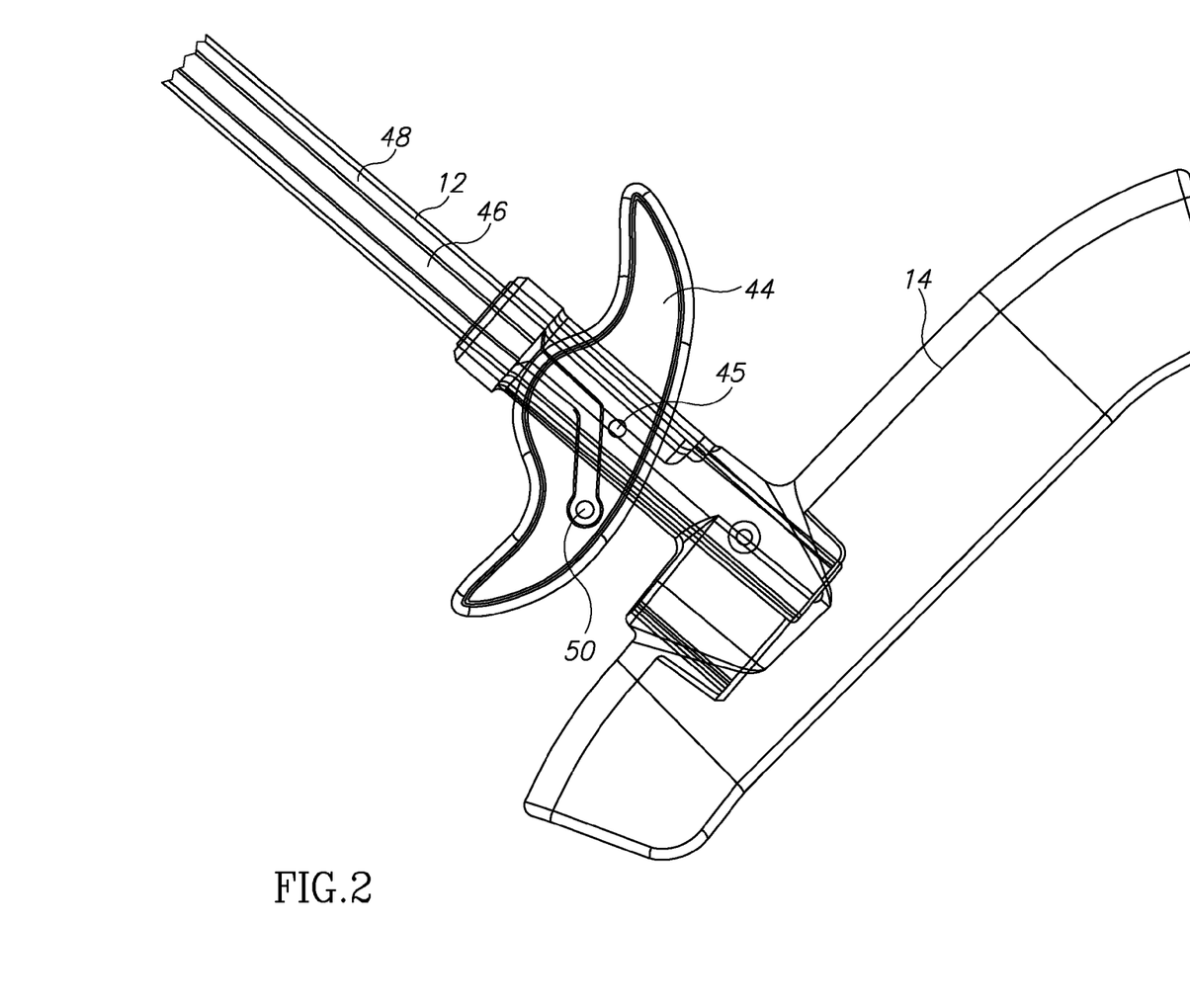
FIG. 2 is a simplified illustration of a proximal portion of the mesh deployment apparatus of FIG. 1, showing a handle and a manipulating member, in accordance with an embodiment of the present invention.

Mesh deployment apparatus 10 may include a deployment rod 12 having a handle 14 at a proximal portion thereof and a roller portion 16 at a distal portion thereof.

Figure 3A:
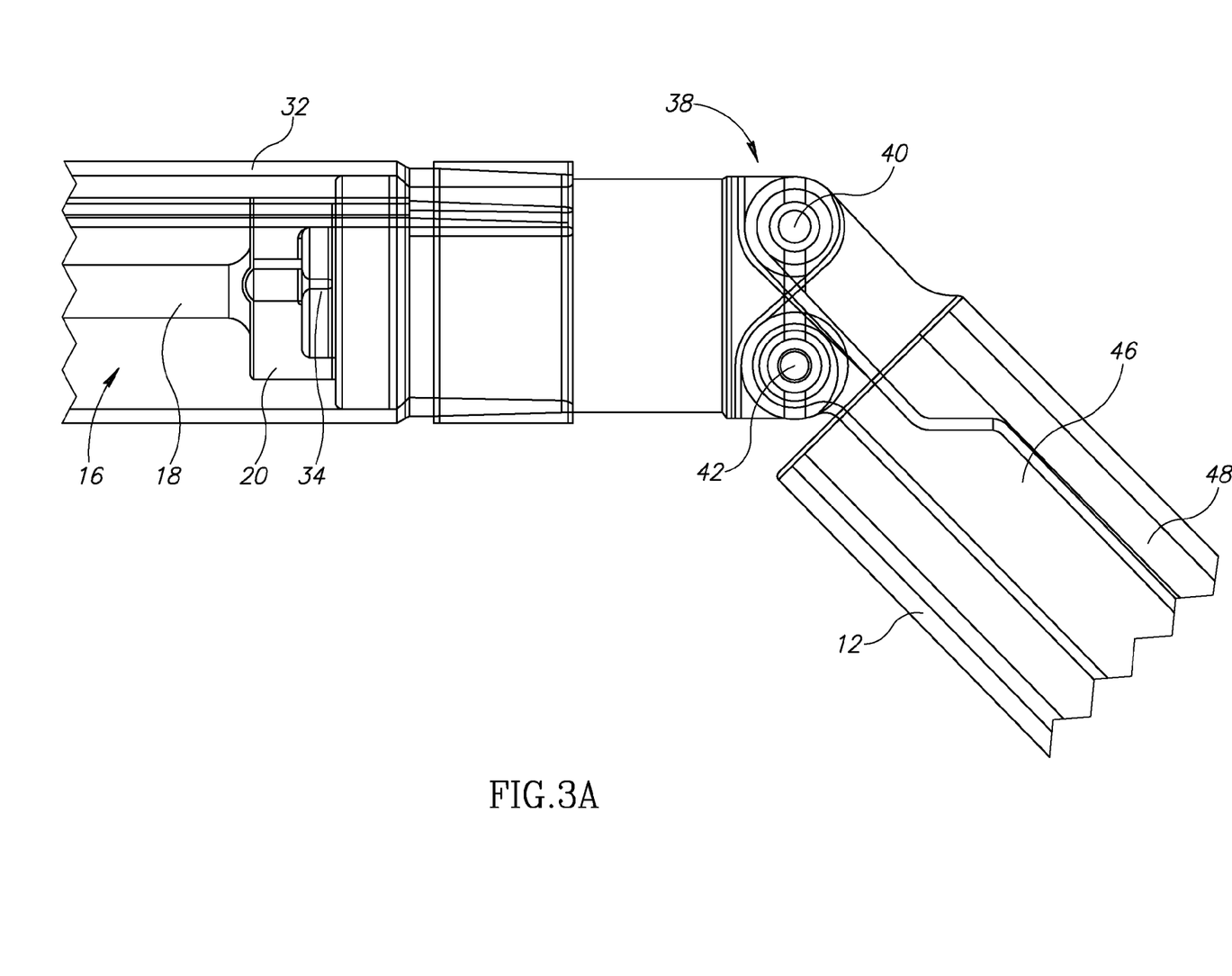
FIGS. 3A and 3B are simplified illustrations of a distal portion of the mesh deployment apparatus of FIG. 1, showing a roller portion, joint and cannula, in accordance with an embodiment of the present invention, in two different angular orientations.
Figure 3B:
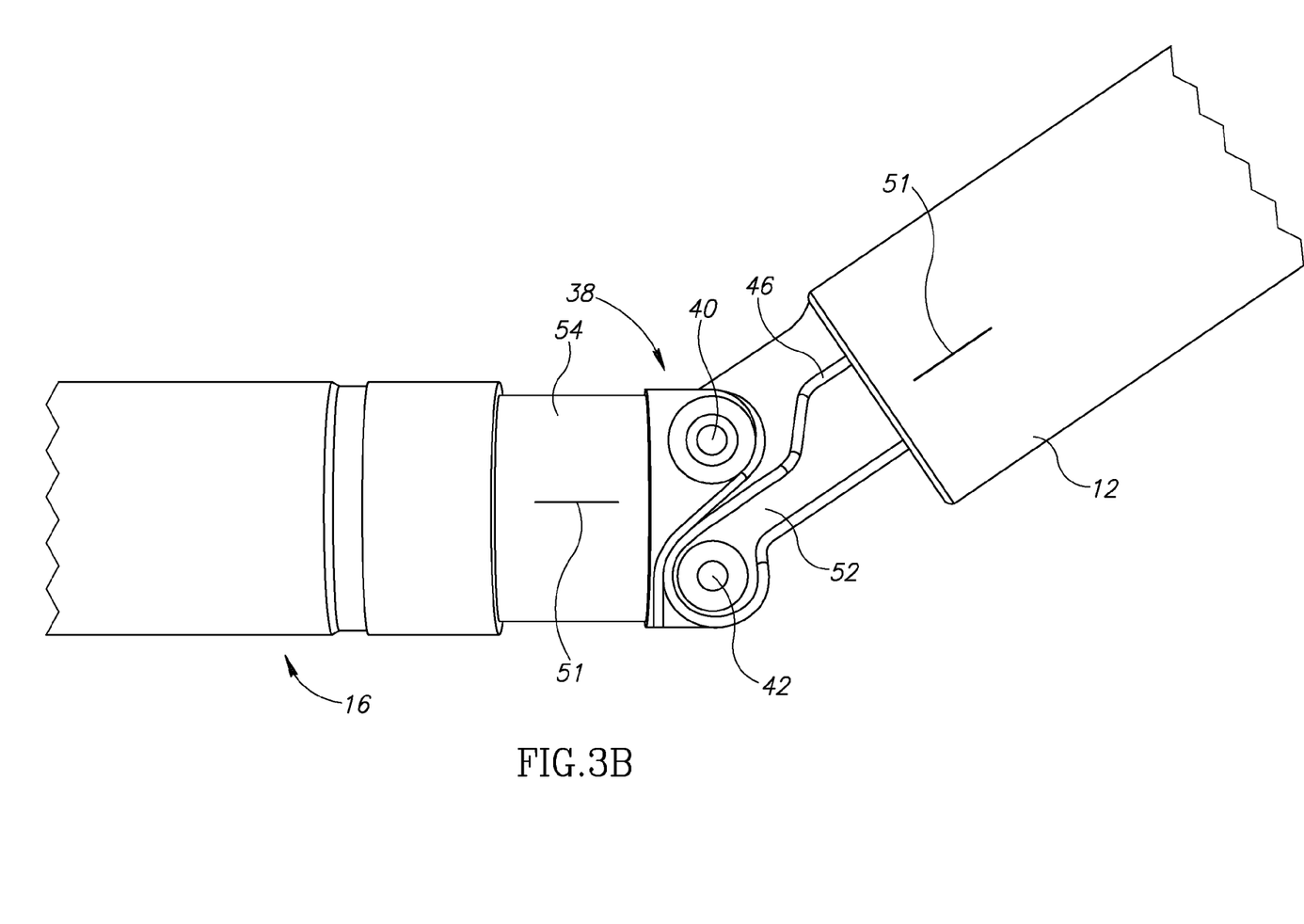
Figure 3C:
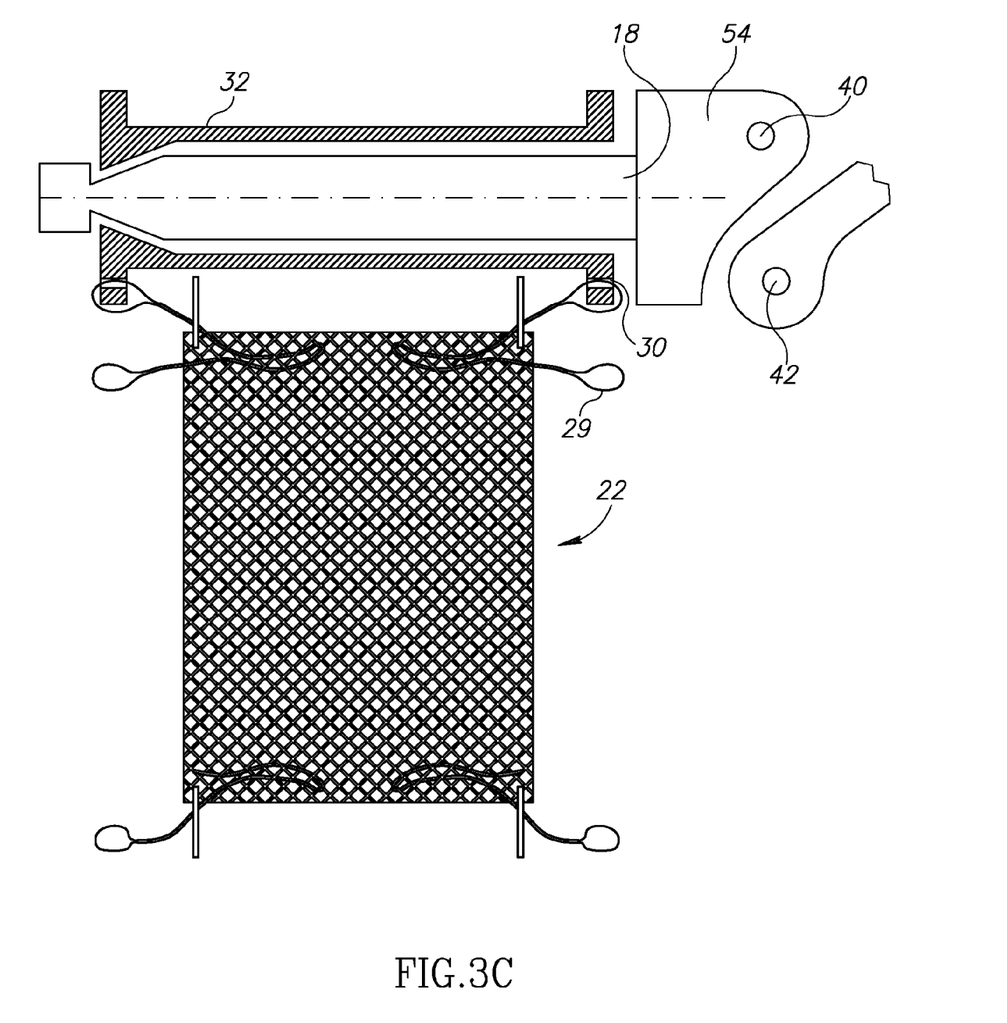
FIG. 3C is a simplified illustration of a distal portion of the mesh deployment apparatus of FIG. 1, showing a roller portion (with a non-rotating shaft), joint and cannula, in accordance with another embodiment of the present invention.
Figure 4A:
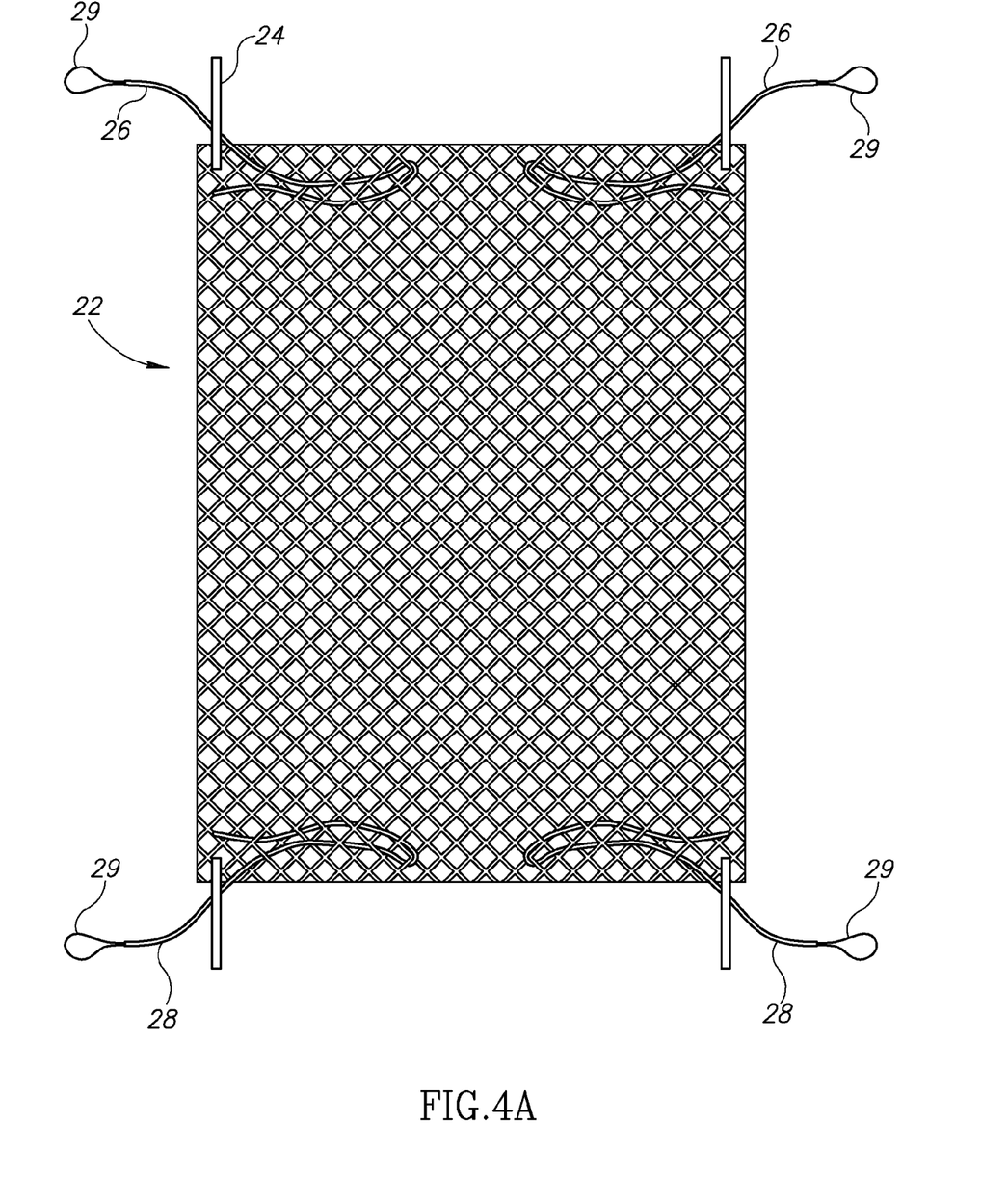
FIG. 4A is a simplified illustration of a mesh which may be deployed with the mesh deployment apparatus of FIG. 1.
Figure 5:
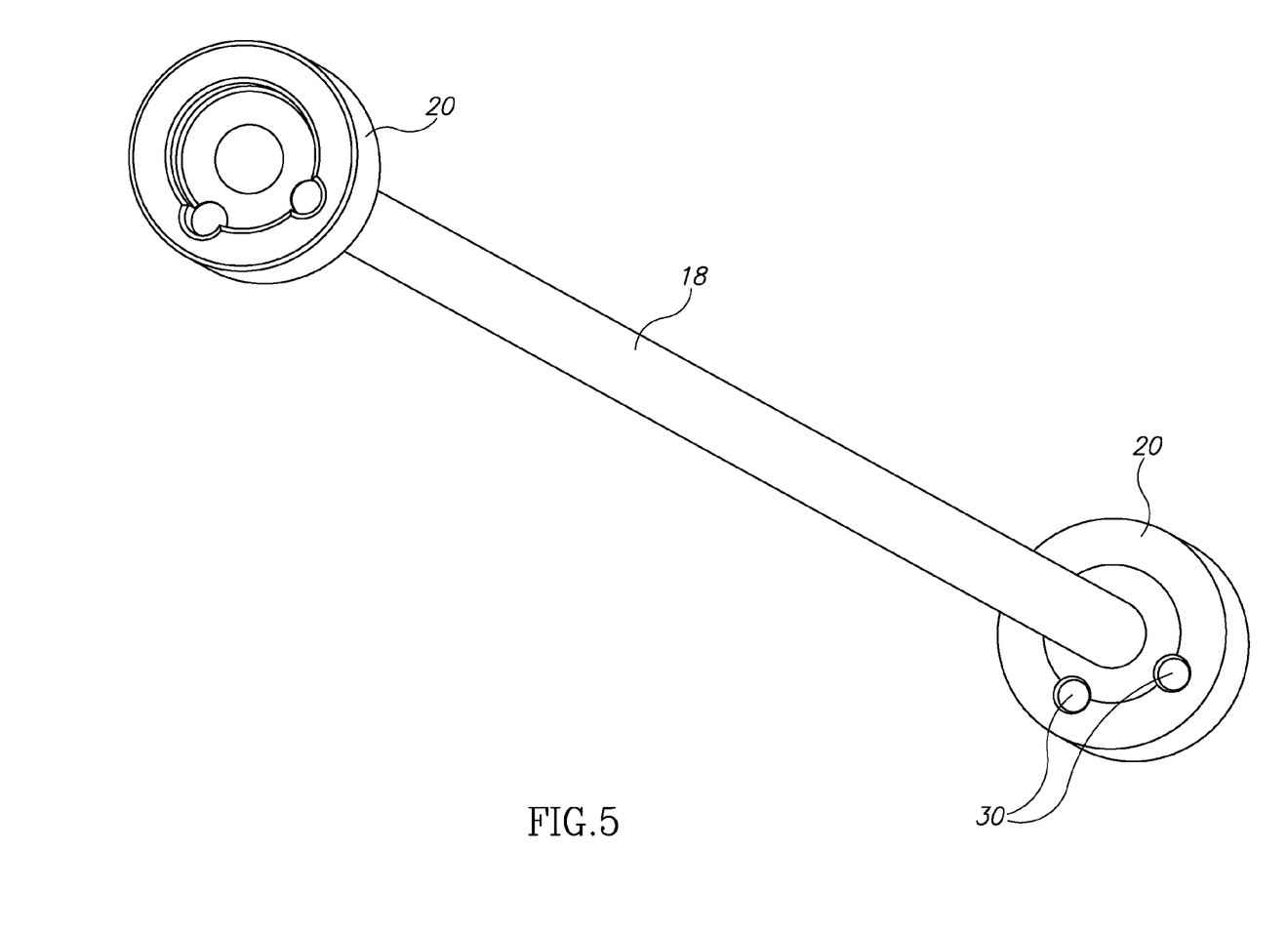
FIG. 5 is a simplified perspective illustration of the roller portion of the mesh deployment apparatus of FIG. 1.

As seen in FIG. 5, roller portion 16 may be constructed of a shaft 18 (which may be a rotating shaft as described below, but not necessarily as seen in the embodiment of FIG. 3C) with end caps 20 at opposite ends of shaft 18. A mesh-sheet 22, which is made of a bio-compatible material as is well known in the art, may be detachably attached to shaft 18 (shaft 18 is thus a mesh-sheet attachment member for attaching a mesh-sheet 22 thereto). As seen in FIG. 4A, mesh-sheet 22 may include a pair of threads 24 that may be tied or otherwise attached to shaft 18 of roller portion 16. The edge of mesh-sheet 22 nearest shaft 18 may have a pair of surgical threads 26 at corners thereof. Likewise, the free or leading edge of mesh-sheet 22 may have a pair of surgical threads 28 at corners thereof. The surgical threads 28 may be provided with needles (not shown) or with loops 29 for easy grasping, such as by a standard "endocatch" tool.

Figure 6:
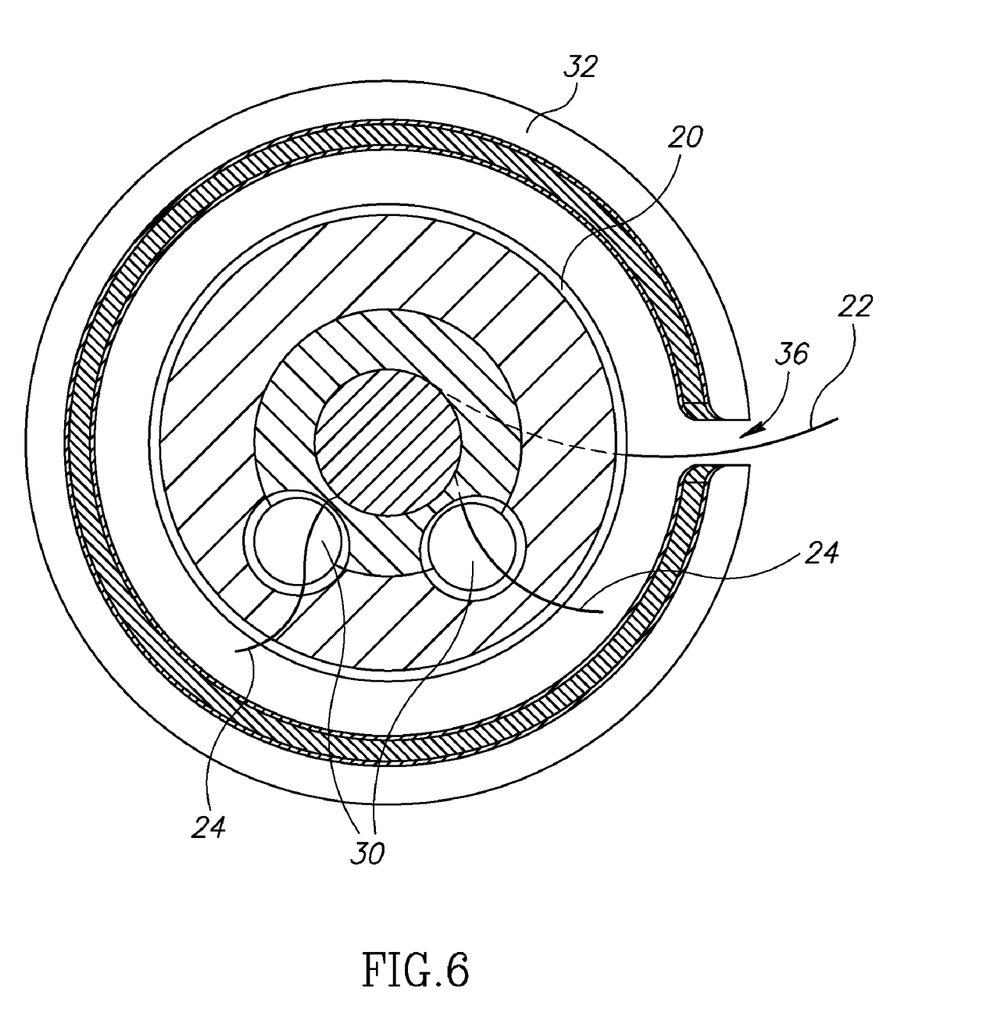
FIG. 6 is a simplified end-view illustration of the roller portion and cannula of the mesh deployment apparatus of FIG. 1.

As seen in FIG. 6, the end caps 20 of roller portion 16 may be formed with apertures 30 for placing therethrough surgical threads 24 of mesh-sheet 22.

As seen in FIGS. 3A and 6, roller portion 16 may be disposed in a cannula 32. As seen in FIG. 3A, shaft 18 of roller portion 16 may be mounted on bearings 34 in cannula 32. Cannula 32 may be provided with a longitudinal slit 36 (FIG. 6) through which mesh-sheet 22 can be drawn. In this manner, mesh-sheet 22 can be easily pulled out of cannula 32 through slit 36 as shaft 18 of roller portion 16 rotates about bearing 34.

Roller portion 16 may be articulated with respect to deployment rod 12 by means of a joint 38. In the non-limiting illustrated embodiment, the joint 38 is made up of two pinned connections between deployment rod 12 and roller portion 16.

A manipulating member 44 may be mounted on deployment rod 12. For example, manipulating member 44 may include a lever arm pivotally mounted on deployment rod 12 at a pivot 45 (FIG. 2), also referred to as pin 45 (because the pivot may be a pinned connection). Manipulating member 44 may be coupled to pin 45 with a linking member 46 that runs through a lumen 48 formed in deployment rod 12. Linking member 46 may include pins 40 and 42 at joint 38. The proximal end of linking member 46 may be secured to manipulating member 44 by a pivot pin 50 (also referred to as a pivot or pin). By pivoting manipulating member 44 about pivot 45 (by pulling either side of manipulating member 44 towards handle 14), the manipulating member 44 moves roller portion 16 about joint 38 to a position wherein roller portion 16 is not collinear with deployment rod 12 (the positions shown in FIGS. 3A and 3B). A zero position of the deployment rod with respect to the roller portion (that is, the deployment rod and the roller portion are collinear) may be marked by alignment of lines 51 (FIG. 3B), thereby simplifying insertion and removal of the device through a trocar.

Reference is particularly made to FIG. 3B. In accordance with an embodiment of the present invention, at a predetermined angular orientation of deployment rod 12 with respect to roller portion 16, a distal end 52 of deployment rod 12 may abut with a proximal end 54 of roller portion 16. This serves as a stop or angular motion limiter, which prevents further angular movement of deployment rod 12 with respect to roller portion 16.

It is noted that other the connection between manipulating member 44 and roller portion 16 may be carried out in other manners. For example, the manipulating member 44 may be connected to roller portion 16 by means of pulleys, gears or other mechanisms.

Mesh deployment apparatus 10 may be a disposable device made of an inexpensive material, or it may be intended for multiple use where it is made of a material suitable for sterilization thereof and where a fresh mesh-sheet 22 may be attached to the roller portion thereof.

The jointed connection of mesh deployment apparatus 10 may enable placing mesh-sheet 22 in a patient with significantly greater dexterity and possibilities of motion that heretofore were not possible.

Figure 4B:
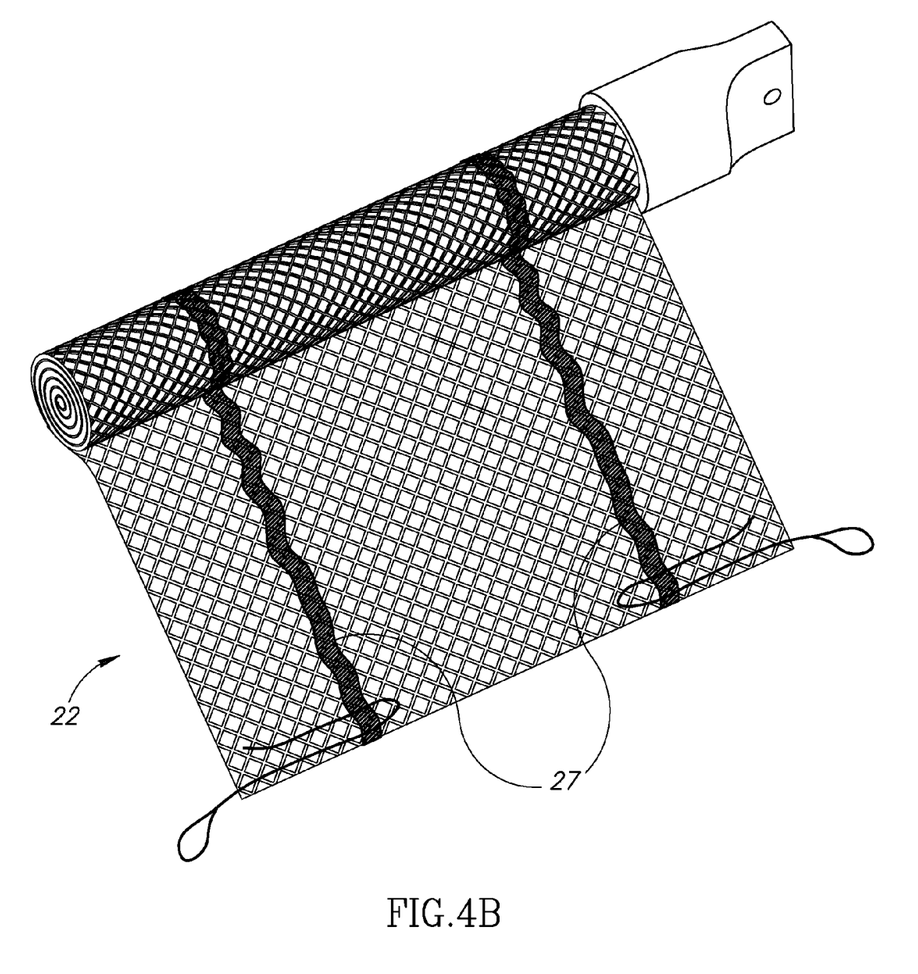
FIG. 4B is a simplified illustration of a mesh which may be deployed with the mesh deployment apparatus of FIG. 1, including adhesive strips of weak adhesive strength.

It is noted that the mesh 22 can come in any kind of container or capsule (shaped or not shaped like the cannula 32 shown above). Furthermore, the mesh 22 does not have to be paid out through the slit 36 in the cannula 32, as described above. Instead, the cannula 32 can be omitted, and the mesh 22 can be simply rolled off the roller portion 16, while the shaft 18 of roller portion 16 turns on its bearings 34. As seen in FIG. 4B, soft adhesive 27 (i.e., not having great adhesive strength) may be used to temporarily bond rolls of the mesh 22 to each other while the mesh 22 is rolled on roller portion 16. This soft adhesive will yield to the pulling force applied by the surgeon to pay out the mesh 22 and easily unroll it from the roller portion 16.

It is noted that the mesh 22 does not necessarily have to come in roll form. The following embodiments show other alternatives to a roll-type mesh. In these embodiments, the mesh is still attached to roller portion 16 of mesh deployment apparatus 10, in which case the "roller portion" may be re-named "application portion" since the mesh does not actually roll off roller portion 16. The term "roller portion" in the claims encompasses such an application portion as well.

Figure 7A:
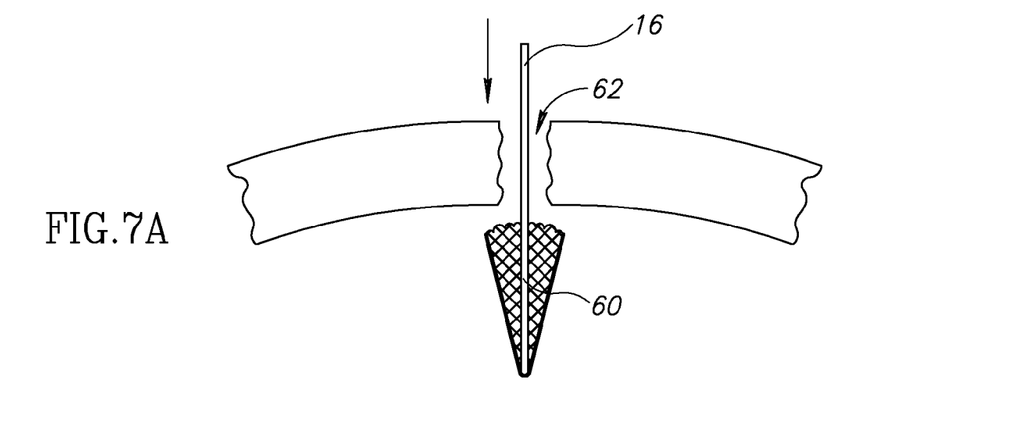
FIGS. 7A, 7B and 7C are simplified illustrations of an umbrella-type mesh, which may be deployed with the mesh deployment apparatus of FIG. 1, in accordance with an embodiment of the present invention.
Figure 7B:
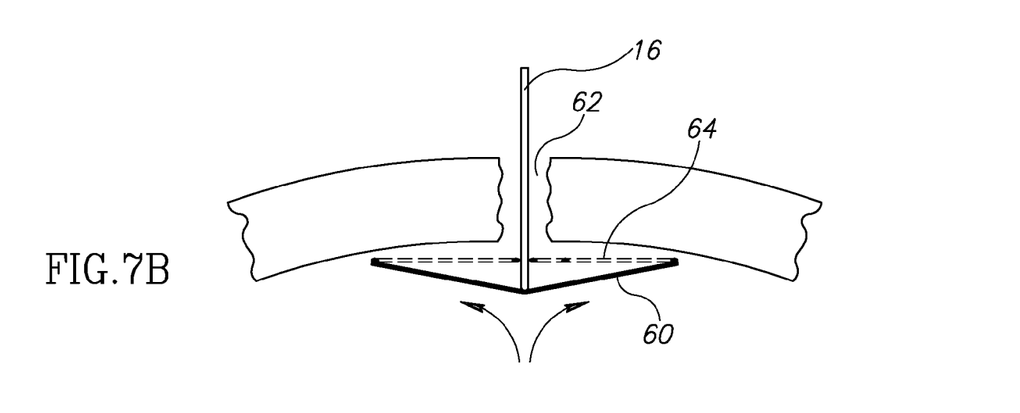
Figure 7C:
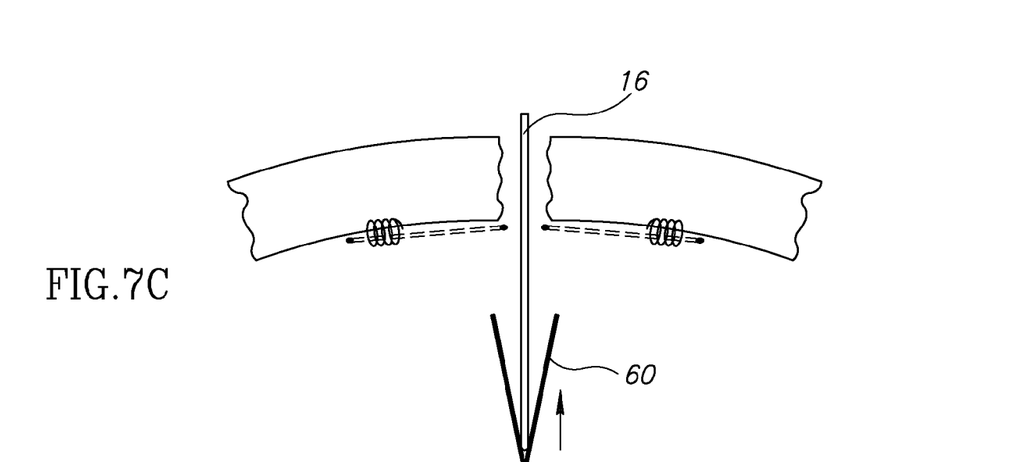
Figure 7D:
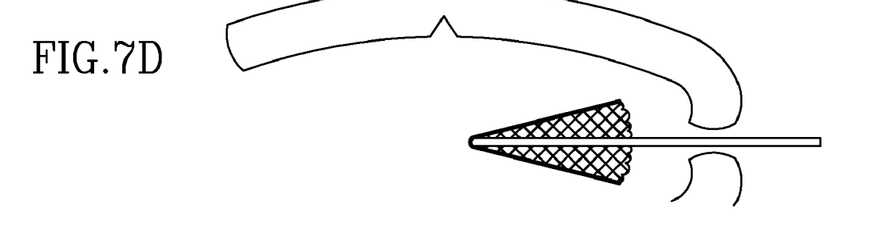
FIGS. 7D-7G are simplified illustrations of an umbrella-type mesh, which may be deployed with the mesh deployment apparatus of FIG. 1, in accordance with another embodiment of the present invention.
Figure 7E:
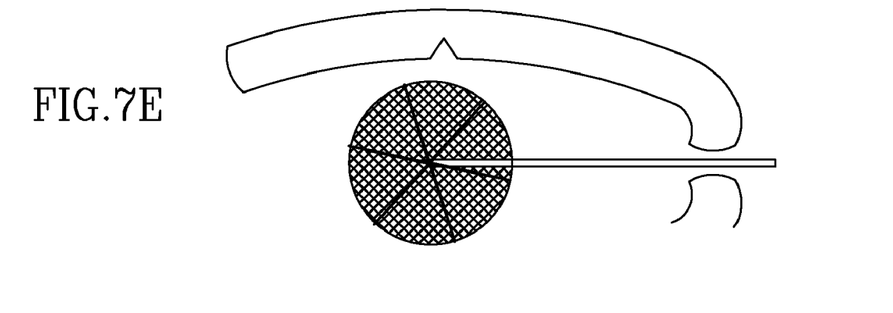
Figure 7F:
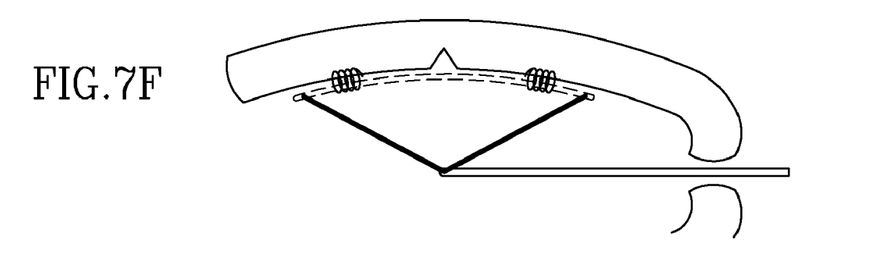
Figure 7G:
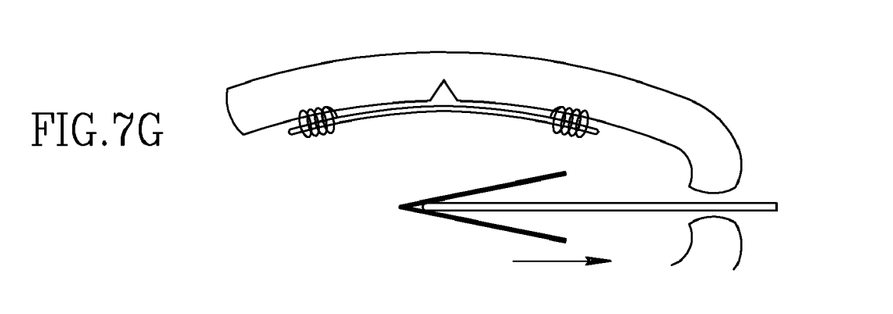

Reference is now made to FIGS. 7A, 7B and 7C, which illustrate an umbrella-type mesh 60. Mesh 60 may be attached to roller portion 16. The roller portion 16 may be inserted through an incision 62 made in a tissue (FIG. 7A) until the mesh 60 is on the far side of the tissue. The mesh 60 may then be spread out like an umbrella, such as by deploying umbrella ribs 64 (e.g., linked to a manipulating member, not shown), as seen in FIG. 7B. The mesh 60 may be attached to the tissue with sutures or any other means, as is known in the art. If needed, mesh 60 may be extracted by closing the umbrella, as seen in FIG. 7C.

Similar deployment (at a different insertion angle) of another umbrella-type mesh is shown in FIGS. 7D-7G.

Figure 8A:
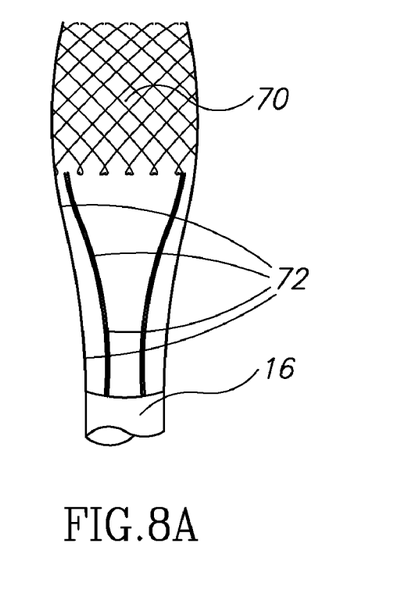
FIGS. 8A and 8B are simplified illustrations of a linear folding spreading mesh, which may be deployed with the mesh deployment apparatus of FIG. 1, in accordance with an embodiment of the present invention.
Figure 8B:
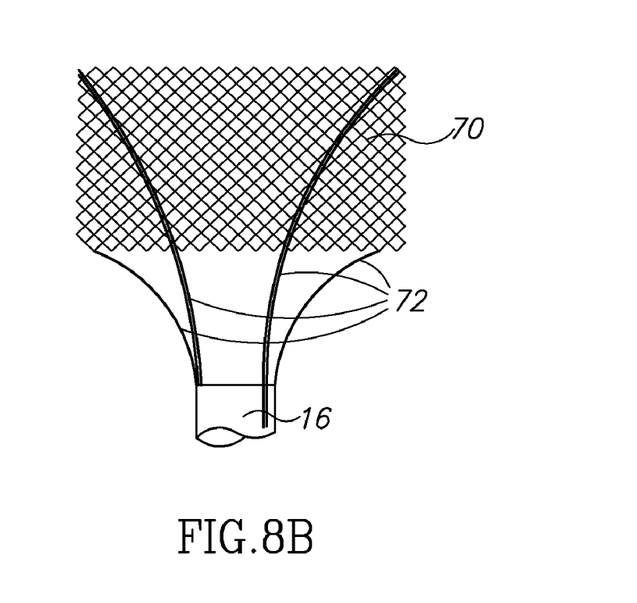

Reference is now made to FIGS. 8A and 8B, which illustrate a linear folding and spreading mesh 70. Mesh 70 may be attached to roller portion 16. A spring-force applicator 72 may be disposed in a hollow portion formed in roller portion 16. The spring-force applicator 72 may include a plurality of leaf springs or other resilient members attached to sides or edges of mesh 70. When the spring-force applicator 72 is pushed distally out of roller portion 16, the leaf springs spring outward, thereby spreading out mesh 70.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Mesh deployment apparatus comprising:
    a deployment rod having a handle at a proximal portion thereof and a roller portion at a distal portion thereof, said roller portion having a shaft and a mesh-sheet attachment member that has a mesh-sheet attached thereto, wherein said roller portion is articulated with respect to said deployment rod by means of a joint; and
    a manipulating member coupled to said roller portion for moving said roller portion about said joint to a position wherein said roller portion is not collinear with said deployment rod, wherein said manipulating member comprises a lever arm pivotally mounted about a pivot on said deployment rod, said lever arm comprising two grasping portions on opposite sides of said pivot and on opposite sides of a longitudinal axis of said deployment rod, wherein said roller portion comprises a pair of end caps at opposite ends of said shaft, said end caps having an extension portion that extends radially outwards from said shaft with through-holes formed in said extension portion, and wherein said mesh-sheet comprises surgical threads that pass through and loop around said through-holes.

2. The mesh deployment apparatus according to claim 1, wherein said manipulating member is coupled to said roller portion with a linking member that runs through a lumen formed in said deployment rod.

3. The mesh deployment apparatus according to claim 2, wherein said linking member rotates about pivots at said joint.

4. The mesh deployment apparatus according to claim 1, further comprising a cannula in which said roller portion is disposed.

5. The mesh deployment apparatus according to claim 4, wherein said roller portion is mounted on bearings in said cannula.

6. The mesh deployment apparatus according to claim 1, wherein said manipulating member manipulates said roller portion at an angle with respect to said deployment rod in a range of ±90°.

7. The mesh deployment apparatus according to claim 1, wherein said through-holes are parallel to said shaft.

8. The mesh deployment apparatus according to claim 1, further comprising an umbrella-type mesh-sheet attached to said roller portion and umbrella ribs for spreading out said mesh-sheet in umbrella fashion.

9. The mesh deployment apparatus according to claim 1, further comprising a linear folding and spreading mesh-sheet and a spring-force applicator disposed in said roller portion and attached to said mesh-sheet.

10. The mesh deployment apparatus according to claim 1, wherein said mesh-sheet comprises surgical threads formed with loops at ends thereof.

11. The mesh deployment apparatus according to claim 1, wherein at a predetermined angular orientation of said deployment rod with respect to said roller portion, a distal end of said deployment rod abuts with a proximal end of said roller portion, so as to prevent further angular movement of said deployment rod with respect to said roller portion.

12. Mesh deployment apparatus comprising:
    a deployment rod having a handle at a proximal portion thereof and a roller portion at a distal portion thereof, said roller portion having a shaft and a mesh-sheet attachment member that has a mesh-sheet attached thereto, wherein said roller portion is articulated with respect to said deployment rod by means of a joint; and
    a manipulating member coupled to said roller portion for moving said roller portion about said joint to a position wherein said roller portion is not collinear with said deployment rod;
    wherein at a predetermined angular orientation of said deployment rod with respect to said roller portion, a distal end of said deployment rod abuts with a proximal end of said roller portion, so as to prevent further angular movement of said deployment rod with respect to said roller portion, wherein said roller portion comprises a pair of end caps at opposite ends of said shaft, said end caps having an extension portion that extends radially outwards from said shaft with through-holes formed in said extension portion and wherein said mesh-sheet comprises surgical threads that pass through and loop around said through-holes.

* * * * *